United States Patent [19]

Caruthers et al.

[11] Patent Number: 5,453,496

[45] Date of Patent: * Sep. 26, 1995

[54] POLYNUCLEOTIDE PHOSPHORODITHIOATE

[75] Inventors: Marvin H. Caruthers; William S. Marshall, both of Boulder, Colo.; Wolfgang Brill, Freiburg, Germany; John Nielsen, Horsholm, Denmark

[73] Assignee: University Patents, Inc., Westport, Conn.

[*] Notice: The portion of the term of this patent subsequent to Jan. 11, 2011 has been disclaimed.

[21] Appl. No.: 138,140

[22] Filed: Oct. 15, 1993

Related U.S. Application Data

[63] Continuation of Ser. No. 793,171, Nov. 18, 1991, Pat. No. 5,278,302, which is a continuation of Ser. No. 545,238, Jun. 27, 1990, abandoned, which is a continuation-in-part of Ser. No. 332,247, Mar. 31, 1989, abandoned, which is a continuation-in-part of Ser. No. 198,886, May 26, 1988, abandoned.

[51] Int. Cl.$^6$ .................. C07H 21/00; C07H 21/02; C07H 21/04
[52] U.S. Cl. .................. 536/24.5; 536/24.3; 536/24.31; 536/24.32
[58] Field of Search .................. 536/24.5, 24.3, 536/24.31, 24.32

[56] References Cited

U.S. PATENT DOCUMENTS

| | | | |
|---|---|---|---|
| 3,451,997 | 6/1969 | Fujimoto et al. | 536/26.71 |
| 3,687,808 | 8/1972 | Merigan et al. | 435/91.3 |
| 3,846,402 | 11/1972 | Eckstein et al. | 536/26.23 |
| 3,853,844 | 12/1974 | Shuman et al. | 536/26.12 |
| 4,373,071 | 2/1983 | Itakura et al. | 536/25.3 |
| 4,415,732 | 11/1983 | Caruthers et al. | 536/26.5 |
| 4,458,066 | 7/1984 | Caruthers et al. | 536/25.34 |
| 4,500,707 | 2/1985 | Caruthers et al. | 536/25.34 |
| 4,668,777 | 5/1987 | Caruthers et al. | 536/26.5 |
| 4,728,730 | 3/1988 | Frey et al. | 536/26.12 |
| 4,806,463 | 2/1989 | Goodchild et al. | 536/23.2 |
| 4,808,708 | 2/1989 | Yoshida et al. | 536/25.34 |
| 5,278,302 | 1/1994 | Caruthers et al. | 536/24.5 |

OTHER PUBLICATIONS

Matsukura et al. Proc. Natl. Acad. Sci. vol. 84, pp. 7706–7710, 1987.
Stel et al. J. Am; Chem. Soc., vol. 106, pp. 6077–6079, 1984.
Eckstein, F. J. Am. Chem. Soc., vol. 92, No. 15, pp. 4718–4723, 1970.
Stein et al. Nucl. Acids Res., vol. 16, No. 8, pp. 3208–3221, 1988.
Froehler, B. C., Tetrahedron Letters, vol. 27, No. 46, pp. 5575–5578, 1986.
Chemical Abstracts (1979), vol. 91, No. 33, p. 623, Abstr. No. 74827a, Sekine et al. J. Org Chem., vol. 44, No. 13, pp. 2325–2326, 1978.

*Primary Examiner*—Douglas W. Robinson
*Assistant Examiner*—Gary L. Kunz
*Attorney, Agent, or Firm*—Yahwak & Associates

[57] ABSTRACT

Oligonucleotides having at least one phosphorodithioate internucleotide linkage. Phosphorodithioate oligonucleotides exhibit stronger antiviral activity than the corresponding phosphorothioate derivatives.

19 Claims, No Drawings

POLYNUCLEOTIDE PHOSPHORODITHIOATE

Research leading to the making of the invention described herein was supported, in part, with federal funds. Accordingly, the United States Government has certain statutory rights to the invention described herein.

This application is a continuation of our earlier filed U.S. patent application 793,171, filed Nov. 18th 1991, now U.S. Pat. No. 5,278,302; which in turn is a continuation of U.S. Pat. application 545,238 filed Jun. 27th 1990, and now abandoned; which in turn is a continuation-in-part application of our earlier filed U.S. patent application 332,247, filed Mar. 31st 1989 and now abandoned; which in turn is a continuation-in-part application U.S. patent application 198,886, filed May 26th 1988 and now abandoned.

For the past several years, various nucleoside and nucleotide analogs have been screened for antiviral activity and, in some cases, observed to be effective. This approach has now been extended to the retroviruses where it has been found that certain analogs such as 3'-azido-2',2'-dideoxythymidine [see Proc. Natl. Acad. Sol. USA 82:7096 (1985)] and the 2',2'-dideoxynucleosides [see Proc. Nat. Acad. Sci. USA 82:1911 (1986)] are effective antivirals because they inhibit retroviral replication and reverse transcriptase activity. An alternative approach by other investigators has been to use oligonucleotides or their analogs as antivirals. For this purpose several oligonucleotides and oligonucleotide analogs having methylphosphonate, phosphorothioate, and phosphoroamidate internucleotide linkages have been tested and shown to be effective antivirals [see Cancer Research 48:2659 (1988)].

Oligonucleotide therapy is being investigated aggressively because, as antivirals, these compounds have known activities in inhibiting primer binding of reverse transcriptase. They activate reverse transcriptase RNase H activity; they block translation of viral RNA genes through hybridization arrest; or they inhibit RNA splicing reactions. The mechanism of inhibition depends upon the choice of oligonucleotide analog and its nucleotide sequence [see Cancer Research 48:2659 (1988)].

High yielding methodologies are currently available for the rapid synthesis of sequence defined polynucleotides having the natural internucleotide linkage [see Science 230:281 (1995), U.S. Pat. Nos. 4,425,732 and 4,458,066], An important step in these methodologies is the oxidation of the intermediate phosphate triester to the naturally occurring phosphate triester with aqueous iodine. These phosphite triesters can also be oxidized, under anhydrous conditions with amines or ammonia and iodine, to yield variable reported amounts of oligonucleotide phosphoramidates, or with sulfur to yield oligonucleotide phosphorothioates [see Chemica Scripta 26:221 (1986), and Tetrahedron Letters 21:4149 (1980)]. Other methods employing H-I-phosphonate internucleotide linkages can also be used to synthesize oligonucleotide phosphoramidates and oligonucleotide phosphorothioates [see Tetrahedron Letters 7:5575 (1986)]. Oligonucleotide methylphosphonates are synthesized from nucleoside methylphosphonamidites [see Tetrahedron 40:95 (1984) and Tetrahedron Letters 25:1437 (1984)].

Recently, methods were developed for synthesizing oligonucleotides containing phosphorodithioate internucleotide linkages (such as those depicted in Examples I, II and III, or in U.S. Pat. No. 5,218,103, the disclosure of which is incorporated in toto herein). These developments have now led to the discovery of the present invention that phosphorodithioate-containing oligonucleotides, a new class of antiviral chemotherapeutic agents, are inhibitors of viral reverse transcriptases.

In general, the oligonucleotide phosphorodithioates according to the present invention, can be represented by the formulae I and II:

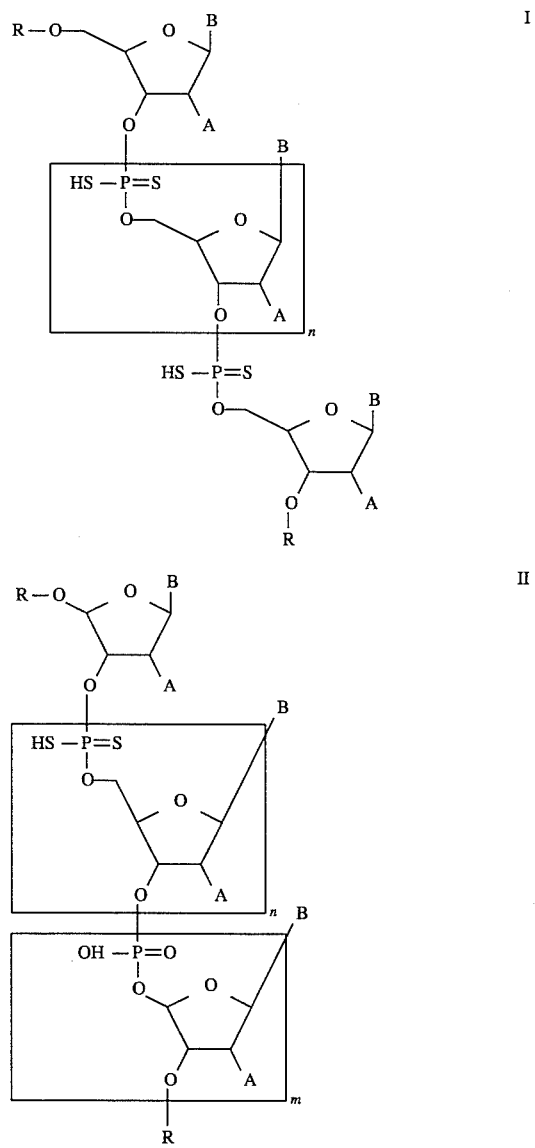

wherein R is H or a blocking group; A is H, OH, halogen, SH, $NH_2$, or azide; B is a nucleoside or deoxynucleoside base (including purines, e.g. adenine, hypoxanthine, guanine, or their derivatives, and pyrimidines, e.g., cytosine, uracil, thymine, or their derivatives) which may be the same or different at each occurrence in the compound; n is an integer from zero to thirty; and m is an integer from one to thirty. If the repeat units represented by m and n are within the same oligonucleotide phosphorodithioate, it is understood that tile repeat units contained within m and n can be positioned in any sequence and that the sum of m and n usually would not exceed thirty. More specifically, these formulae are intended to include any permutation of phosphorodithioate and normal diester linkages. Thus, these formulae should be interpreted as encompassing a series of dithioate linkages (n) followed by a series of normal phosphate diester linkages (m) or encompassing a series of alternating or interspersed phosphorodithioate linkages within art oligonucleotide polymer. Accordingly, for clarity of disclosure the compounds of the present invention may also be generically depicted as an oligonucleotide having at least one phosphorodithioate linkage substituted for the normally occurring phosphate diester linkage in the oligonucleotide. That is, oligonucleotides according to the present invention can be represented by the formula:

R-O-[N-O-L-O-N]$_t$-O- R wherein N represents a nucleoside moiety (that is a purine or pyrimidine base in glycosidic linkages with a sugar) of the formula

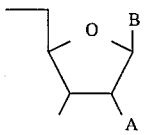

wherein A, B and R are as defined previously; wherein L is a phosphate internucleotide linkage of the formula

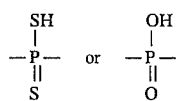

wherein at least one L in the formula is

and wherein t is an integer from 1 to 60, preferably from 1 to 30.

The new class of chemotherapeutic compounds according to the present invention and represented by the formulae above are oligonucleotides having a 3'–5' phosphate diester linkage, ribose and deoxyribose sugars, purine and pyrimidine bases, and the nucleosides and deoxynucleosides linked to phosphorus through oxygen covalently joined at the 3' and 5'-carbons of the sugars. Compound I has two sulfur atoms bonded to each phosphorus whereas compound II has at least one phosphorus bonded to two sulfur atoms and one phosphorus bonded to two oxygens while each remaining phosphorus is bonded to either two sulfurs or two oxygens. Thus it can be seen that compound I depicts an oligonucleotide having exclusively phosphorodithioate internucleotide linkages whereas compound II depicts an oligonucleotide having at least one phosphorodithioate internucleotide linkage and one phosphate internucleotide linkage with the remainder being either phosphorodithioate or naturally occurring phosphate diester linkages. In each of Formula I or II, B may be the same or different base for each occurrence.

The chemical synthesis of compound I is completed using appropriately protected deoxynucleoside or nucleoside phosphorothioamidites as synthons, preferably a deoxynucleoside or nucleoside joined covalently to a silica support. Activation of the synthon is most easily accomplished with tetrazole. The reaction sequence is then completed by oxidation with sulfur, acylation of unreacted, silica bonded deoxynucleoside or nucleoside, and the subsequent selective removal of appropriate protecting groups. This cycle can then be used repetitively in order to extend the oligonucleotide so that it contains as many as 32 nucleosides (i.e., when n equals 30).

A similar sequence may be used to prepare compound II. In this sequence, two synthons, a deoxynucleoside or nucleoside phosphoramidite and a deoxynucleoside or nucleoside phosphorothioamidite, are used to prepare an oligonucleotide having the phosphate and phosphorothioate internucleotide linkages with m plus n equal to thirty.

In order to provide a more detailed understanding of the present invention, the following examples and procedures are provided. These depict the formation of compounds I and II, demonstrate how these compounds inhibit viral reverse transcriptases, and provide a more complete understanding and illustration of the present invention. They are, however, examples, and as such are not intended in any manner to limit the scope of the present invention.

The procedure outlined in the following Example I may also be used to produce dipyrrolidinylchlorophosphine, and bis(dimethylamino) chlorophosphine. Preparation of thiophosphoramidites of the formula

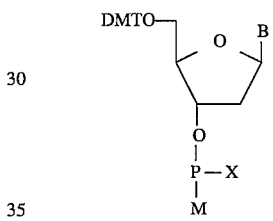

wherein B may be 1-thyminyl, 1-(N-4-benzoylcytosinyl), 9-(N-6-benzoyladeninyl), or 9-(N-2-isobutyrylguaninyl); DMT is di-p-anisylphenylmethyl (dimethoxytrityl); M may be S-(4-chlorobenzyl) or S-(2,4-dichlorobenzyl); and X may b N,N-dimethylamino or pyrrolidinyl wherein the further use of these compounds to prepare oligonuoleotides having phosphorodithioate internucleotide linkages are presented in the remaining examples.

EXAMPLE I

Bis(dimethylamino)chlorophosphine was prepared by adding tris(dimethylamino)-phosphine (36.3 ml, 32.6 g, 0.2 mole) and trichlorophosphine (8.7 ml, 13.7 g, 0.1 mole) to anhydrous ether (100 ml). After stirring for 3 hours at room temperature, solvent was removed by concentration in vacuo at room temperature. The product was then distilled (b.p. 72°–75 ° C.) at reduced pressure (approx. 16 mm Hg) using a water aspirator to yield 30 g. of product.

Example II describes the synthesis of 5'-O-dimethoxytrityl-N 4-benzoyldeoxycytidyl, 1-3'-S(4-chlorobenzyl) phosphorothiopyrrolidinite, and its further use to prepare oligonucleotides having phosphorodithioate internucleotide linkages. The same procedure can be used for the other suitably protected deoxynucleosides. Similarly the same procedure is useful for all the 2,4-dichlorobenzyl and 4-chlorobenzyl protected sulfur derivatives of the N,N-dimethylamino and pyrrolidinyl amidites. Table I summarizes the $^{31}$P-NMR data for all these amidites.

Using the deoxycytidine phosphorothioamidite made in the following Example II, Compound Ia, wherein n is 12, B is cytosine and A is hydrogen was prepared. Compound Ia therefore has the following structure where C represents deoxycytidine and x represents the phosphorodithioate internucleotide linkage.

d(CxCxCxCxCxCxCxCxCxCxCxCxC)

EXAMPLE II

5'-O-Dimethoxytrityl-N4-benzoyldeoxycytidine (317 mg, 0.5 mmol) was dissolved in a mixture of acetonitrile (2 ml) and triethylamine (1 ml) under argon. Bispyrrolidinylchlorophosphine (124 mg, 0.6 mmol) was added which was followed by the immediate formation of a precipitate. After 5 minutes stirring at room temperature, 4-chlorobenzylmercaptan (159 mg, 1 mmol) was added to the reaction mixture and the solution, including the precipitate, was concentrated to a glass in vacuo at room temperature. The glass was resuspended in acetonitrile (2 ml). The $^{31}$P-NMR spectrum of the reaction mixture indicated that the major phosphorus containing product was the diastereoisomers of the thioamidite (161.5, 159.7 ppm). Minor impurities were an adduct of bispyrrolidinylchlorophosphine and 4-chlorobenzylmercaptan (107.0 ppm) and hydrolysis products (12.4 ppm). Triethylamine was next added to the reaction mixture. The solution was diluted with deacidified ethylacetate (50 ml) and extracted with aqueous saturated sodium bicarbonate (50 ml×2) and brine. The combined aqueous solutions were back-extracted with deacidified ethylacetate (10 ml). The organic solutions were combined, dried for 1 hour over sodium sulfate in the presence of 10% (volume) triethylamine, filtered, and the filtercake washed with 5 ml deacidified ethylacetate. The organic solution was then concentrated in vacuo to a white foam. This foam was dissolved in toluene (10 ml) containing 1% triethylamine and the product isolated by precipitation into n-pentane:triethylamine (999:1, v/v). After filtration, the product was dried in vacuo over phosphorus pentoxide and potassium hydroxide and isolated in 83.1% yield (741 mg).

Using a deoxynucleoside attached covalently to a silica based polymer support through the 3'-hydroxyl (in accordance with the teaching of U.S. Pat. No. 4,458,066, the disclosure of which is incorporated herein), synthesis of deoxyoligonucleotides containing phosphorodithioate linkages proceeded according to the reaction sequence outlined below wherein (P) represents the polymer support.

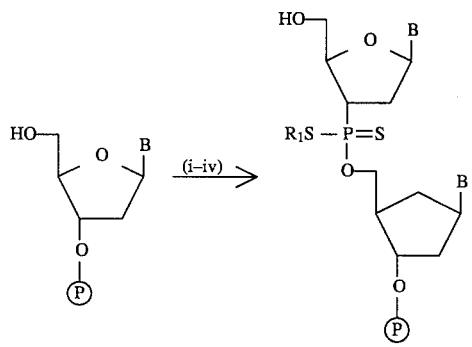

Wherein $R_1$ is a blocking group. More specifically, the over-all reaction sequence for the making of the present invention is depicted as:

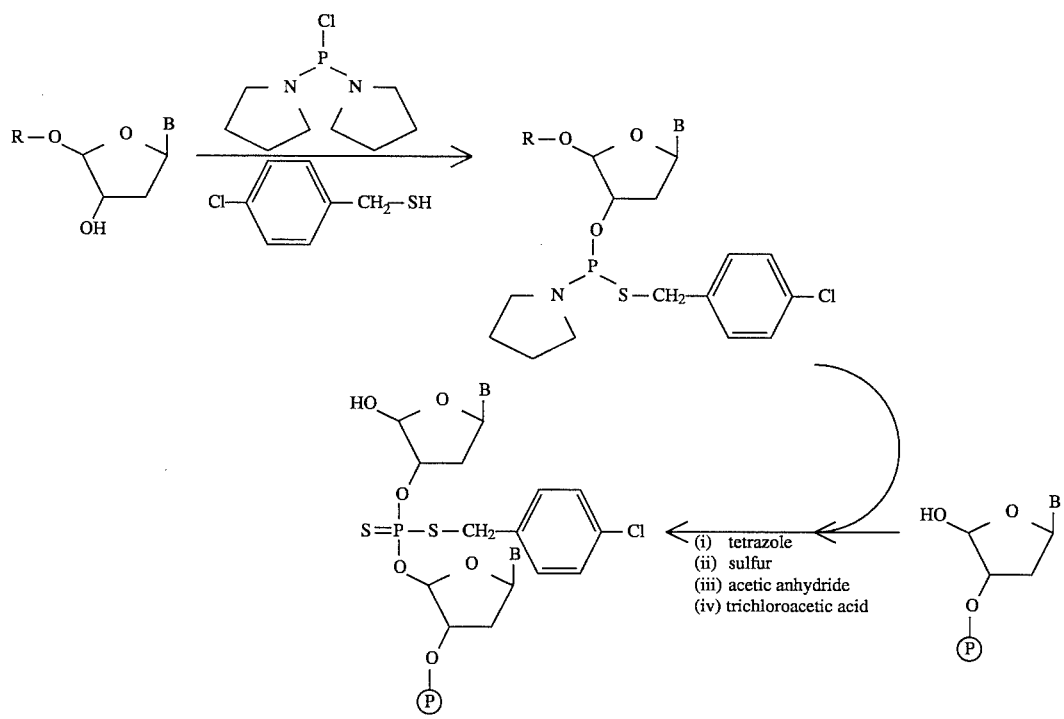

wherein R is a protecting group as shown in the following examples, B is a nucleoside or deoxynucleotide base, and (P) is a silica-based support as defined below.

In general, synthesis began by reacting a dry acetonitrile solution of any thiophosphoramidite according to Example II (10 equivalents) and tetrazole (50 equivalents) with 1 μmole of deoxynucleoside on silica for 30 seconds (i) followed by a 400 sec oxidation with 5% sulfur in pyridine:carbon disulfide (1:1, v/v) (ii). Coupling was performed twice to ensure high yields (greater than 98%). Acylation of unreacted deoxynucleoside (iii), detritylation (iv) and various washes were the same as those described previously for synthesizing natural DNA from deoxynucleoside phosphoramidites (U.S. Pat. No. 4,415,732 and Science 230:281 (1085)). Repetitions of this cycle an additional twelve times led to the synthesis of compound Ia. Deoxyoligonucleotides such as compound II having both phosphorodithioate and phosphate internucleotide bonds may be synthesized when both deoxynucleoside phosphorothioamidites and deoxynucleoside phosphoramitides are used during synthesis.

Synthetic deoxyoligonucleotides were isolated free of protecting groups using a two-step protocol (thiophenol:t-ethylamine:dioxane, 1:1:2, v/v/v for 24 h followed by conc. ammonium hydroxide for 15 h), and then purified to homogeneity by standard procedures (polyacrylamide gel electrophoresis and reverse phase hplc). 31 P-NMR spectra of phosphorodithioate DNA indicated that this synthesis protocol yielded DNA containing phosphorodithioate internucleotide linkages.

TABLE I

31P-NMR Characterization of Deoxynucleoside Phosphorothioamidites

| Base (B) | Amine (X) | Mercaptan (M) | $^{31}$P-NMR$^a$ (δ) |
|---|---|---|---|
| T | pyrrolidinyl | 2,4-dichlorobenzyl | 164.8;161.8 |
| T | pyrrolidinyl | 4-chlorobenzyl | 164.2;161.0 |
| T | dimethylamino | 4-chlorobenzyl | 172.3;170.5 |
| T | dimethylamino | 2,4-dichlorobenzyl | 172.1;170.4 |
| $C^{Bz}$ | pyrrolidinyl | 2,4-dichlorobenzyl | 165.1;162.6 |
| $C^{Bz}$ | pyrrolidinyl | 4-chlorobenzyl | 161.8;159.9 |
| $C^{Bz}$ | dimethylamino | 4-chlorobenzyl | 1.71;170.7 |
| $C^{Bz}$ | dimethylamino | 2,4-dichlorobenzyl | 172.0;171.0 |
| $A^{Bz}$ | pyrrolidinyl | 2,4-dichlorobenzyl | 163.8;162.7 |
| $A^{Bz}$ | pyrrolidinyl | 4-chlorobenzyl | 163.5;162.3 |
| $A^{Bz}$ | dimethylamino | 4-chlorobenzyl | 171.8;170.9 |
| $A^{Bz}$ | dimethylamino | 2,4-dichlorobenzyl | 171.7;170.9 |
| $G^{Bz}$ | pyrrolidinyl | 2,4-dichlorobenzyl | 163.9;160.9 |
| $G^{Bz}$ | pyrrolidinyl | 4-chlorobenzyl | 163.4;161.6 |
| $G^{Bz}$ | dimethylamino | 4-chlorobenzyl | 171.5;169.5 |
| $G^{Bz}$ | dimethylamino | 2,4-dichlorobenzyl | 171.9;169.6 |

$^a$indicates $^{31}$P-NMR were recorded on a Brucker WM-250 with 85% aqueous $H_3PO_4$ as external standard.
T, $C^{Bz}$, $A^{Bz}$, and $G^{iB}$ refer to thymine, N-benzoylcytosine, N-benzoyladenine, and N-isobutyrylguanine respectively;
R1 is dimethyltrityl,
A is hydrogen Syntheses are described in the following Example III for Compounds IIa, IIb and IIc wherein m and n are variables for IIa, IIb, and IIc, R is hydrogen, B is cytosine, and A is hydrogen. Compounds IIa, IIb and IIc have the following structures wherein C represents deoxycytidine, x represents the phosphorodithioate internucleotide linkage, and p tile naturally occurring phosphate internucleotide linkage.

IIa: d(CpCxCpCpCpCpCpCpCpCpCpCpCxCpC)

IIb: d(CpCpCpCpCpCpCxCpCpCpCpCpCpC)

IIc: d(CxCpCxCpCxCpCxCpCxCpCxCpC)

Synthesis of Dinucleoside Phosphorodithioate Triesters of the formula:

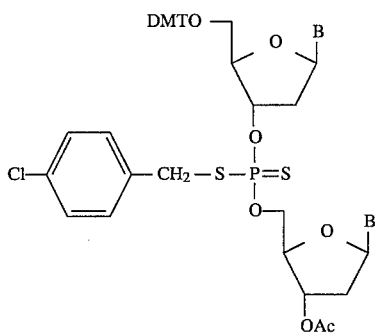

wherein B may be 1-thyminyl, 1-(N-4-benzoylcytosinyl), 9-(N-6-benzoyladeninyl), or 9-(N-2-isobutyrylguaninyl); DMT is di-p-anisylphenylmethyl (dimethoxytrityl); and Ac is acetyl and the further conversions of the deoxydicytidine derivative to deoxycytidine oligodeoxynucleotides having phosphorodithioate internucleotide linkages at various positions are presented in this example.

EXAMPLE III

A. The synthesis of a thymidine dinucleotide having a phosphorodithioate Internucleotide linkage is described below:

5'-O-dimethoxytritylthymidine (1.2 g. 2.21 mmol) was dried by co-evaporation with anhydrous THF and then dissolved in THF (10 ml) and triethylamine (0.46 ml, 3.3 mmol). Bis-(diisopropylamino)-chlorophosphine (650 mg, 2.44 mmol) was added and the solution stirred at room temperature. After 35 minutes, the precipitate was removed by filtration and washed with THF (1 ml). The combined filtrates containing the deoxynucleoside phosphorodiamidite were pooled, concentrated in vacuo, and redissolved in acetonitrile (5 ml). 3'-O-acetylthymidine (639 mg, 2.25 mmol) and tetrazole (142 mg, 2.0 mmol) were dried by co-evaporation with THF (10 ml), redissolved in acetonitrile (5 ml), and added to the acetonitrile solution of the deoxynucleoside phosphorodiamidite. After stirring for 45 minutes at room temperature, the reaction mixture was diluted with dichloromethane (75 ml), extracted with an aqueous sodium bicarbonate solution (5% w/v), dried over sodium sulfate, filtered, and concentrated in vacuo to a gum. The product was then purified by column chromatography (100 ml silica, ethylacetate :dichloromethane :-triethylamine; v/v/v) to yield 1.59 g of the deoxydinucleoside phosphoramidite (1.66 mmol, 75%).

The deoxynucleoside phosphoramidite was then converted to the deoxydinucleoside phosphorodithioate triester. The deoxynucleoside phosphoramidite (1.59 g, 1.66 mmol) was dissolved in acetonitrile (7 ml). 4-chlorobenzylmercaptan (1.0 ml, 1.2o g, 7,6 retool) and tetrazole (281 mg, 4.01 mmol) were added and the reaction mixture stirred at room temperature for 30 minutes. A solution of sulfur in toluene:2,6-lutidine (19:1, v/v, 10 ml containing 4 mmol atomic sulfur) was added and the resulting solution stirred for 10 minutes. The reaction mixture was diluted with ethylacetate (75 ml), extracted with an aqueous sodium bicarbonate solution (5%, w/v), dried over sodium sulfate, filtered and concentrated in vacuo to an oil. The oil was dissolved in ethylacetate (40 ml) and triturated with hexanes (200 ml) to give a crude product as a white powder. Purification by silica column chromatography (100 ml silica, 2–12% methanol in dichloromethane as % eluant) yields the deoxydinucleoside phosphorodithioate triester (1.59 g, 1.52 retool, 91%).

Removal of the 3'-O-acetyl group (0.15M t-butylamine in methanol, 0 °C., 10 h) yields a deoxydinucleoside phosphorodithioate that can be used for DNA synthesis (1.26 g, 1.28 mmol, 84%). The deoxydinucleoside phosphorodithioate is converted to the 3'-phosphoramidite and then used to synthesize DNA on a polymer support.

B. The synthesis of deoxycytidine oligomers containing phosphorodithioate internucleotide linkages is described below:

5'-O-DimethoxytrityI-N-toluoyldeoxycytidine was prepared by a minor modification of a published procedure (Tetrahedron 37:363 (1981)). Deoxycytidine hydrochloride (10 mmol, 2.64 g) was co-evaporated twice with anhydrous pyridine and resuspended in pyridine (50 ml). Trimethylchlorosilane (7.5 ml, 59 mmol) was added and the mixture stirred for 45 minutes at room temperature. o-Toluoyl chloride (1.44 ml, 11 mmol) was added and the reaction stirred for two additional hours. The reaction mixture was chilled in an ice bath, treated with methanol (10 ml) and 25% ammonium hydroxide (20 ml) for 30 min, and the suspension removed by filtration. The resulting solution was concentrated to dryness in vacuo. The resulting solid was suspended in 40 ml dichloromethane:methanol (8:2) and the insoluble salts removed by filtration. The filtrate was concentrated in vacuo to an oil, reconcentrated twice in vacuo after addition of pyridine and redissolved in pyridine (50 ml). After addition of 0.9 equivalents of dimethoxytrityl chloride (3.05 g), the reaction mixture was stirred for 30 rain at 0 °C. and 30 rain at room temperature. Dimethoxytritylchloride (0.3 equivalents) was added and stirring was continued for 30 minutes. The reaction was quenched by addition of methanol (1 ml) and the solution concentrated in vacuo. The resulting oil was dissolved in dichloromethane (75 ml) and extracted sequentially with aqueous 5% sodium bicarbonate (w/v) and brine. The combined organic phase was dried over sodium sulfate, filtered, concentrated to dryness in vacuo, dissolved in dichloromethane:pyridine (99.5:0.5, v/v) and the produce purified by column chromatography (50 g silica, dichloromethane:methanol:pyridine gradient from 0 to 3% methanol; 400 ml each). Fractions containing the 5'-O-dimethoxytrityl-N-toluoyldeoxycytidine were pooled, concentrated in vacuo, redissolved in ethylacetate and precipitated into pentane (5.01 g, 7.7 mmol, 77%).

3'-O-Phenoxyacetyl-N-toluoyldeoxycytidine was prepared by minor modification of a published procedure (Tetrahedron Letters 4273 (1968)). 5'-O-DimethoxytrityI-N-toluoyldeoxycytidine (1.94 g, 3 mmol) and phenoxyacetic anhydride (1.72 g, 6 mmol) was dissolved in tetrahydrofuran (50 ml). After addition of pyridine (173 ml, 9 mmol), the solution was stirred for 14 hours at room temperature and then concentrated in vacuo. The resulting oil was dissolved in dichloromethane (75 ml), extracted twice with 5% aqueous sodium bicarbonate (100 ml, w/v) and the combined aqueous phases extracted with dichloromethane (50 ml). The product in the combined organic phase was dried over sodium sulfate, filtered, concentrated to dryness in vacuo, redissolved in ethylacetate and precipitated in pentane. The solid corresponding to totally protected deoxycytidine was dissolved in dichloromethane: methanol (8:2, v/v) and chilled in an ice bath. A solution of p-toluenesulfonic acid (2121 g, 12 mmol) in dichloromethane:methanol (50 ml, 8:2, v/v) was added and the solution stirred for one hour in an ice bath. The reaction was then quenched by addition of 5% aqueous sodium bicarbonate. The organic layer was extracted with brine and the aqueous phase re-extracted with dichloromethane (60 ml). The combined organic phase was dried over sodium sulfate, filtered and concentrated to dryness in vacuo. The resulting oil was dissolved in dichloromethane and the product purified by silica gel column chromatography (20 g of silica, elution with dichloromethane and dichloromethane:methanol (1 to 3% methanol). Fractions containing 3'-O-phenoxyacetyl-N-toluoyldeoxycytidine were pooled, concentrated to an oil, and the product isolated as a precipitate by addition of ethylacetate (1.20 g, 83%).

Deoxydicytidine phosphoramidite in protected form was prepared using the following procedure:

5'-O-DimethoxytrityI-N-toluoyldeoxycytidine (647 mg, 1 mmol) was co-evaporated three times with THF, dissolved in THF (5 ml) and triethylamine (0.21 ml, 1.5 mmol) and reacted with bis (N,N-diisopropylamino) chlorophosphine (320 mg, 1.2 mmol). After 90 minutes under argon, the reaction mixture was filtered under argon pressure to remove insoluble salts. The salts were washed with THF (2 ml). The filtrate was concentrated to dryness and the product redissolved in acetonitrile (2 ml). 3'-O-phenoxyacetyl-N-toluoyldeoxycytidine (527 mg, 1.1 mmol) and tetrazole (70 mg, 1 mmol) were suspended in acetonitrile (4 ml) and the above solution, including 1.5 ml acetonitrile used to wash the flask, was added. The reaction mixture was stirred under argon for 105 min. and then poured into ethylacetate:triethylamine (99:1, v/v, 25 ml), the organic phase was dried over sodium sulfate, filtered, and concentrated in vacuo. Purification was achieved by silica gel column chromatography (25 g silica, elution with hexanes:dichloromethane:triethylamine, 50:50:0.5, 400 ml, 45:55:0.5, 200 ml, 40:60:0.5, 200 ml, and 35:65:0.5, 100 ml). Product fractions were pooled, concentrated in vacuo, and precipitated into pentane (67%).

Deoxydicytidine phosphorodithioate was prepared using the following procedure:

The deoxydicytidine phosphoroamidite as prepared in the previous procedure (1.4.0 g, 1.12 retool) was dissolved in acetonitrile (5 ml) (previously flushed with helium to avoid oxygen oxidation of thiophosphite) and 4-chlorobenzylmercaptan (0.5 ml, 3.7 mmol) and tetrazole (190 mg, 2.7 retool) were added. The solution was stirred under argon for 30 min and, without isolation, the resulting thiophosphite was oxidized to tile phosphorodithioate triester by addition of 5 ml of a 0.4M solution of sulfur in toluene:lutidine (19:1, v/v). Based on 31 P-NMR analysis, oxidation was complete after 10 minutes. The reaction mixture was diluted with ethylacetate (75 ml), extracted twice with 5% aqueous sodium bicarbonate (75 ml each), and the combined aqueous phases back-extracted with ethylacetate (50 ml). The combined organic phases were dried over sodium sulfate, filtered, and concentrated in vacuo to an oil. The oil was dissolved in a minimal amount of dichloromethane, diluted with ethylacetate to approximately 40 ml, and the product precipitated by addition of 200 ml hexanes. The white precipitate was filtered, redissolved in dichloromethane, and the solution concentrated to dryness. The product was purified by silica gel column chromatography (40 g silica gel, elution with dichloromethane:hexanes:triethylamine, 66:33:0.03, 400 ml and dichloromethane:triethylamine, 100:0.03, 200 ml). Fractions containing the completely protected product were pooled, concentrated in vacuo, redissolved in dichloromethane, and precipitated into pentane (60%).

The 3'-O-phenoxyacetyl protecting group was removed using the following procedure:

The completely protected deoxydicytidine phosphorodithioate triester (355 mg, 0.264 mmol) was dissolved in acetonitrile (3 ml) and diluted with methanol (9 ml). After chilling the solution in an ice bath, t-butylamine in methanol(0.3M, 12 ml) was added and the reaction mixture stirred for 90 rain in an ice bath. The reaction solution was concentrated to dryness and the product purified by silica gel column chromatography (30 g silica, elution with dichloromethane:triethylamine, 100:0.03, 100 ml followed by 200 ml each of dichloromethane:methanol:triethylamine, 99:1:0/03, 98:2:0/03 and 97:3:0.03). Product fractions were concentrated to dryness, redissolved in dichloromethane, and precipitated into pentane (95% yield).

The deoxydicytidine phosphorodithioate was next converted to the 3'-phosphoramidite which is useful as a synthon for synthesizing DNA containing dithioate internucleotide linkages. The deoxydicytidine phosphorodithioate having a free 3'-hydroxyl (304 mg, 0.251 mmol) was dissolved in acetonitrile (5 ml). Bis(diisopropylamino)-β-cyanoethoxyphosphine (1 21 mg, 0.402 mmol) and tetrazole (20 mg, 0.286 mmol) were added under argon and the solution stirred for 2 hours. After quenching with ethylacetate:triethylamine (19.5:0.5) and diluting further with ethylacetate (20 ml), the reaction mixture was extracted twice with 2M triethylammonium bicarbonate (13 ml each) and the aqueous phase back-extracted with ethylacetate:triethylamine (19.5:0.5). The organic layer was dried over sodium sulfate, filtered, and concentrated to an oil in vacuo. The resulting oil was redissolved in dry ethylacetate and precipitated into pentane (87% yield).

Deoxycytidine pentadecamers containing phosphorodithioate internucleotide linkages at selected sites were synthesized using the deoxydicytidine phosphorodithioate synthons having a 3'-O-(β-cyanoethyl)-N,N-diisopropylphosphoramidite moiety as described above and 5'-O-dimethoxytrityl-N-benzoyldeoxycytidine-3'-O-(β-cyanoethyl)-N,N-diisopropylphosphoramidite. The standard phosphoramidite synthesis methodology was used (U.S. Pat. Nos. 4,415,732 and 4,458,066). The average coupling efficiency was set at 99% (3 minute coupling time, 0.2 μmol deoxycytidine on controlled pore glass as a support). The products were freed of protecting groups by treatment with a solution of thiophenol:triethylamine:dioxane (1:1:2, v/v/v) at room temperature for 6 hours (some product remains as the S-protected dithioate (5- 10%) when analyzed by gel electrophoresis and concentrated ammonium hydroxide at 55 ° C. (15 hours). Purification of the final product was by either polyacrylamide gel electrophoresis or high performance liquid chromatography. Using deoxycytidine as one embodiment of the present invention, three pentadecamers having phosphorodithioate linkages at specific positions were synthesized and have the following sequence:

d(CpCxCpCpCpCpCpCpCpCpCpCxCpC)

d(CpCpCpCpCpCxCpCpCpCpCpCpC)

d(CxCpCxCpCxCpCxCpCxCpCxCpC)

wherein x represents a dithioate linkage and p represents the naturally occurring phosphate internucleotide linkage.

The ability of deoxyoligonucleotide homopolymers made in accordance with the present invention to inhibit viral reverse transcriptases was tested using an assay whereby a deoxyoligonucleotide primer (P) was extended enzymatically using a reverse transcriptase enzyme, deoxynucleotide triphosphates (dNTP), and a deoxyoligonucleotide as template (T). The system is as follows:

```
P:   5'-GpApTpTpCpApGpCpTpApGpTpCpCpA
T:   3'-CpTpApApGpTpCpGpApTpCpApGpGpTpApGpCpApTpApGp
TpGpTpCpApApApC
                                dATP, dTTP, dCTP, dGTP
                                Reverse transcriptase
                                ± deoxyoligonucleotide inhibitor
P: 5'-GpApTpTpCpApGpCpTpApGpTpCpCpApTpCpGpTpApTpCpApCpAp
GpTpTpTpG
T: 3'-CpTpApApGpTpCpTpApTpCpApGpGpTpApGpCpApTpApGpTpGpTp
CpApApApC
```

Thus it can be seen that the assay involves DNA repair synthesis. Deoxynucleotide triphosphates are incorporated into the primer strand using reverse transcriptase as the DNA polymerizing enzyme. Two reverse transcriptases, the human immunodeficiency virus type I reverse transcriptase (HIV-I reverse transcriptase) and avian myeloblastosis virus reverse transcriptase (AMV reverse transcriptase), and a normal cellular polymerase, the large fragment of E. coli DNA polymerase I (Klenow polymerase), were used in this assay. Several deoxyoligonucleotide homopolymers having combinations of phosphorodithioate internucleotide linkages (Ia, IIa, IIb, IIc, V and VI), one deoxyoligonucleotide homopolymer having phosphorothioate internucleotide linkages (IIIa), and one deoxyoligonucleotide homopolymer having natural phosphate diester linkages (IVa) were tested as inhibitors of the reverse transcriptases. Additional deoxyoligonucleotides with heterosequences and having phosphorodithioate (VII, VIII and IX) or phosphorothioate (X) internucleotide linkages were also tested as inhibitors of the reverse transcriptases. Compounds IIia, X, and IVa were prepared using published procedures (U.S. Pat. Nos. 4,415, 731 and 4,458,066; JACS 106:6077 (1984); and Biochemistry 3443 (1984)). These compounds have the following sequences where internucleotide linkages are represented by x for phosphorodithioate, p for the naturally occurring phosphate, and for the phosphorothioate:

Ia: d(CxCxCxCxCxCxCxCxCxCxCxCxC)

IIa: d(CpCxCpCpCpCpCpCpCpCpCpCxCpC)

IIb: d(CpCpCpCpCpCpCpCpCpCpCpCpC)

IIc: d(CxCpCxCpCxCpCxCpCxCpCxCpC)

IIIa: d(C-C-C-C-C-C-C-C-C-C-C-C-C-C)

IVa: d(CpCpCpCpCpCpCpCpCpCpCpCpC)

V: d(TxTxTxTxTxTxTxTxTxTxTxTxT)

VI: d(AxAxAxAxAxAxAxAxAxAxAxAxA)

VII: d(GxAxTxTxCxAxGxCxTxAxGxTxCxCxA)

VIII: d(GxCxTxAxCxGxGxCxTxCxGxCxTxG)

IX: d(CxTxGxTxTxCxGxGxGxCxGxCxCxA)

X: d(C-T-G-T-T-C-G-G-G-C-G-C-C-A)

The primer (P) and template (T) deoxyoligonucleotides were also synthesized using published procedures (U.S. Pat. Nos. 4,415,732 and 4,458,066).

Assays for measuring the inhibition of DNA repair synthesis with phosphorodithioate containing DNA were completed using the following procedure:

EXAMPLE IV

Primer (12 μM) and template 10 μM) in a solution of Tris hydrochloride (Tris. HCl, 50 mM, pH 8.3), MgCl$_2$ (10 mM), and dithiothreitol (DTT, 5 mM) were warmed at 90 ° C. for five minutes and then cooled on ice to 0 ° C. 5'-$^{32}$P labeled primer was approximately 0.5% of total primer. Aliquots of primer-template were then mixed with other components to yield assay solutions (20 μl) having the following composition: template (1 μM), primer (1.2 μM), tris-HCl (50 mM, pH 8.3), MgCl$_2$ (10 mM), KCI (50 mM), DTT (5 mM), dTTP (250 μM), dCTP (250 μM), dGTP (250 μM), and inhibitor oligonucleotide at variable concentrations from zero to 70 μM. Reactions were started by adding AMV reverse transcriptase (7.2 nM), HIV-I reverse transcriptase (10 nM or 50 nM) or Klenow fragment (200 nM). Assays were incubated at 37 ° C. for 15 minutes, quenched by adding formamide to 50%, and analyzed by electrophoresis on a 15% denaturing polyacrylamide gel. Radioactive bands containing polymerized primer and unextended primer were cut from the gels, dried and analyzed in a scintillation counter. The results are presented in Table 2.

TABLE 2

SUMMARY OF THE ID$_{50}$ VALUES FOR PHOSPHOROTHIOATED DEOXYOLIGONUCLEOTIDES

| Inhibitor | HIV-I Reverse Transcriptase | ID$_{50}$ Values AMV Reverse Transcriptase | Klenow Fragment |
|---|---|---|---|
| Ia | 60 nM | 250 nM | >>800 nM* |
| IIa | 30 μM | ND | ND |
| IIb | 75 μM | ND | ND |
| IIc | 2 μM | 11 μM | ND |
| IIIa | 2 μM | 42 μM | ND |
| IVa | >36 μM** | >70 μM* | ND |
| V | 30 nM | | |
| VI | 75 nM | | |
| VII | 10 nM | | |
| VIII | 10 nM | | |
| IX | 4.4 nM | | |
| X | 126 nM | | |

ND indicates the result was not determined;
ID$_{50}$ indicates the concentration of inhibitor where the reaction proceeds to 50% of the uninhibited reaction;
*indicates that inhibition was observed at these concentrations whereas HIV-I reverse transcriptase was completely inhibited; and
**indicates that only 7% inhibition at 36 μM of inhibitor IVa The results listed in Table 2 can be summarized as follows. Compound la, a phosphorodithioate containing deoxyoligocytidine, is a very potent inhibitor of HIV-I reverse transcriptase (ID$_{50}$=60 nM) and is about 33 fold more inhibitory than IIIa, a phosphorothioate linked deoxyoligocytidine of about the same length. Similarly la inhibits a second reverse transcriptase, AMV reverse transcriptase, approximately 168 fold more effectively than IIIa. Compounds V and VI which correspond to the dithioate derivatives of oligodeoxythmidine (V) and oligodeoxyadenosine (VI) are also very potent inhibitors of HIV reverse transcriptase. The oligodeoxythymidine derivative (V) is even a more potent inhibitor than the corresponding oligodeoxycytidine derivative (Ia). Also of considerable interest was the discovery that la did not inhibit a normal cellular polymerase, the large fragment of E. coli DNA polymerase I or Klenow fragment, even at 800 nM. At this concentration, HIV-I reverse transcriptase is completely inhibited. Two other discoveries merit comment. First normal deoxyoligocytidine, compound IVa, is noninhibitory at concentrations where both HIV-I reverse transcriptase and AMV reverse transcriptase are completely inhibited by Ia. Also a comparison of the results with HIV-I reverse transcriptase and Ia, IIa, IIb, and IIc shows that the extent of inhibition correlates directly with the number of phosphorodithioate linkages present in the deoxyoligonucleotide.

Each of the compounds designated V to IX are either 14 or 15 nucleotides in length, and all have exclusively dithioate internucleotide linkages. Compounds V and VI are homopolymers having polydeoxythymidine and polydeoxyadenosine sequences, respectively. Compound IX is of special significance as it has a sequence identical to tile corresponding human lysine transfer RNA that is used naturally by the HIV reverse transcriptase to initiate viral RNA synthesis [see Cell 40:9 (1985)]. The ID$_{50}$ value for compound IX (4.4 nM) represents essentially 50% inhibition of the total HIV reverse transcriptase in the reaction mixture. Thus, this indicates that the enzyme is being titrated in the test system and therefore a much lower concentration of compound IX can be used with a continued inhibitory effect. Compound X has the same sequence as IX but contains all phosphorothioate internucleotide linkages. As can be seen from the data in Table 2, compound IX containing all dithioate linkages is at least 30 fold more inhibitory than X which has the thioate linkages. Sequences VII and VIII correspond to the primer sequence as used in this assay (VII) and an oligonucleotide (VIII) having tire same base composition as IX but a different sequence. As can be seen from the data in Table 2, both VII and VIII are less inhibitory than IX. Thus this data shows that the DNA sequence corresponding to human lysine transfer RNA (IX), the RNA that binds to the primer binding site on the HIV genome, and is used to initiate DNA synthesis, is the most inhibitory dithioate containing deoxyoligonucleotide.

These results demonstrate that we have discovered a new class of potent chemotherapeutic agents for the treatment of viruses. These reagents are the phosphorodithioate containing deoxyoligonucleotides which are strongly inhibitory toward reverse transcriptases with ID50 values less than the 60 nM range. This means that these reagents are at least 33 fold more inhibitory than the phosphorothioate class of oligonucleotides. As was the case with phosphorothioate oligonucleotides which are also inhibitory against HIV-I reverse transcriptase [see Cancer Research 48:2659 (1988), and Biochemistry 28:1340 (1989)], it is to be expected this new class of chemotherapeutic agents, the phosphorodithioate oligonucleotides, to be inhibitory towards viruses containing reverse transcriptases such as HIV-I. Our results also demonstrate the discovery that the most inhibitory oligonucleotide is a hetero sequence that has a DNA sequence corresponding to the 3'-terminal sequence of the human lysine tRNA located at the primer binding site of the HIV genome.

The compounds according to the present invention may be administered transdermally to mammalian host species having pathological conditions brought about by viruses, and other causative agents having a reverse transcriptase requirement for their transportation into the mammalian cell (infection), replication, or genetic expression. In these instances, the compounds may be formulated in suitable compositions determined by the intended means of administration, according to methods and procedures well-known to those skilled in the art. These compounds according to the present invention may be further modified to enhance transport into cells or to target specific tissues or organs by linkage of the compounds with steroids, sugars, peptides, nucleotides, lipids, or their derivatives. As used herein, the term "transdermal" is to be considered in its broadest meaning, that is administration across an epithelial layer of cells. As such, the term is appropriately used to designate topical, oral, pernasal, intravenous, intramuscular, and other methods of administration. For example, the compounds suitable for use in this invention may be formulated either individually or with other "active agents" or compounded with various conventional bases into preparations such as creams, ointments, gels, lotions, tablets, or pharmaceutical solutions for injection or sprays depending upon the desired mode of administration to the individual. In manufacturing these preparations, the composition may also be mixed with conventional thickening agents, emollients, surfactants, pigments, perfumes, preservatives, fillers, and emulsifiers, all of which are well known and conventionally used in the formulation of transdermal preparations. Typically, these nonactive ingredients; will make up the greater part of the final preparation. Preferably, the compositions would be manufactured to allow for slow-release or timed-release delivery. Dosage to be given would, of course, depend upon the route of administration, the administration vehicle, and the degree and severity of the condition to be treated. In each instance, a minimal amount sufficient for bringing about the inhibition of the desired reverse transcriptase enzyme would be administered.

Thus while we have illustrated and described the preferred embodiment of our invention, it is to be understood that this invention is capable of variation and modification and we therefore do not wish to be limited to the precise terms set forth, but desire to avail ourselves of such changes and alterations which may be made for adapting the invention to various usages and conditions. Accordingly, such changes and alterations are properly intended to be within the full range of equivalents, and therefore within the purview of the following claims.

Having thus described our invention and the manner and process of making and using it in such full, clear, concise, and exact terms so as to enable any person skilled in the art to which it pertains, or with which it is most nearly connected, to make and use the same;

We claim:

1. An oligonucleotide of at least 2 nucleotides in length and having a 5'-terminal nucleotide of the formula:

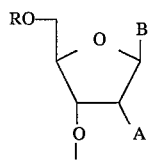

and a 3'-terminal nucleotide of the formula:

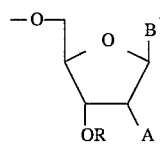

and wherein the 5'- and 3'-terminal nucleotides of oligonucleotides containing at least three nucleotides are separated by a series of nucleotides of the formula:

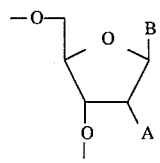

wherein each individual R is hydrogen or a blocking group; wherein each individual A is hydrogen, hydroxyl, halogen, SH, $NH_2$, azide or $OR_4$ wherein $R_4$ is a blocking group; wherein each individual B is a purine or pyrimidine nucleotide base; and wherein each nucleotide in the oligonucleotide is connected to the preceding and following nucleotide by an internucleotide linkage; and wherein the oligonucleotide has at least one phosphorodithioate internucleotide linkage having the structure:

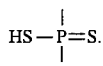

2. An oligonucleotide according to claims 1 wherein A is hydrogen.

3. An oligonucleotide according to claim 1 wherein A is hydroxyl.

4. An oligonucleotide according to claim 1 wherein B is selected from the group consisting of cytosine, adenine, guanine, and thymine.

5. An oligonucleotide according to claim 4 which is a homopolymer.

6. An oligonucleotide according to claim 5 in which each B is cytosine.

7. An oligonucleotide according to claim 6 which is d(CxCxCxCxCxCxCxCxCxCxCxCxCxC) wherein C is cytosine and x is a phosphorodithdate internucleotide linkage.

8. An oligonucleotide according to claim 6 which is d(CpCxCpCpCpCpCpCpCpCpCpCpCxCpC) wherein C is cytosine, p is a phosphate internucleotide linkage, and x is a phosphorodithioate internucleotide linkage.

9. An oligonucleotide according to claim 6 which is d(CxCpCxCpCxCpCxCpCxCpCxCpCxCpC) wherein C is cytosine, p is a phosphate internucleotide linkage, and x is a phosphorodithioate internucleotide linkage.

10. An oligonucleotide according to claim 6 which is d(TxTxTxTxTxTxTxTxTxTxTxTxT) wherein T is thymine, and x is a phosphorodithioate internucleotide linkage.

11. An oligonucleotide according to claim 5 which is d(AxAxAxAxAxAxAxAxAxAxAxAxA) wherein A is adenine, and x is a phosphorodithioate internucleotide linkage.

12. An oligonucleotide according to claim 6 which is a heteropolymer.

13. An oligonucleotide according to claim 12 which is d(GxAxTxTxCxAxGxCxTxAxGxTxCxCxA) wherein G is guanine, A is adenine, T is thymine, C is cytosine, and x is a phosphorodithioate internucleotide linkage.

14. An oligonucleotide according to claim 12 which is d(GxCxTxAxCxGxGxCxTxCxGxCxTxG) wherein G is guanine, A is adenine, T is thymine, C is cytosine, and x is a phosphorodithioate internucleotide linkage.

15. An oligonucleotide according to claim 12 which is d(CxTxGxTxTxCxGxGxGxCxGxCxCxA) wherein G is guanine, A is adenine, T is thymine, C is cytosine, and x is a phosphorodithioate internucleotide linkage.

16. An oligonucleotide according to claim 1 wherein the oligonucleotide contains from 2 to 62 nucleotides.

17. An oligonucleotide according to claim 1 wherein R is hydrogen.

18. An oligonucleotide according to claim 1 wherein R is a blocking group.

19. An oligonucleotide according to claim 1 which is of at least 2 nucleotides in length, and wherein each B is independently varied and wherein one B is a purine and the second B is a pyrimidine.

* * * * *